(12) United States Patent
Simkins

(10) Patent No.: US 12,082,601 B2
(45) Date of Patent: Sep. 10, 2024

(54) PERACETIC ACID MONITORING AND CONTROL SYSTEM

(71) Applicant: Polygon US Corporation, North Andover, MA (US)

(72) Inventor: David Simkins, Stuart, FL (US)

(73) Assignee: Polygon US Corporation, North Andover, MA (US)

( * ) Notice: Subject to any disclaimer, the term of this patent is extended or adjusted under 35 U.S.C. 154(b) by 346 days.

(21) Appl. No.: 17/398,216

(22) Filed: Aug. 10, 2021

(65) Prior Publication Data
US 2022/0061361 A1  Mar. 3, 2022

Related U.S. Application Data

(60) Provisional application No. 63/071,443, filed on Aug. 28, 2020.

(51) Int. Cl.
| | |
|---|---|
| A61L 2/00 | (2006.01) |
| A01N 37/16 | (2006.01) |
| A22C 17/08 | (2006.01) |
| A22C 21/00 | (2006.01) |
| A23B 4/12 | (2006.01) |
| A23B 4/30 | (2006.01) |
| A23L 3/00 | (2006.01) |
| A23L 3/3517 | (2006.01) |
| A23L 3/3589 | (2006.01) |
| A61L 2/18 | (2006.01) |

(Continued)

(52) U.S. Cl.
CPC .............. *A23L 3/003* (2013.01); *A01N 37/16* (2013.01); *A22C 17/08* (2013.01); *A22C 21/0061* (2013.01); *A23B 4/12* (2013.01); *A23B 4/30* (2013.01); *A23L 3/001* (2013.01); *A23L 3/3517* (2013.01); *A23L 3/3589* (2013.01); *A61L 2/18* (2013.01); *B01F 23/49* (2022.01); *B01F 35/2132* (2022.01); *B01F 35/2211* (2022.01); *B01F 35/718051* (2022.01); *F24F 11/0001* (2013.01); *A23V 2002/00* (2013.01); *A61L 2202/14* (2013.01); *B01F 23/483* (2022.01); *B01F 2101/04* (2022.01); *F24F 2011/0002* (2013.01)

(58) Field of Classification Search
CPC .............................. A61L 2202/14; A23L 3/003
USPC .................................................. 422/305, 306
See application file for complete search history.

(56) References Cited

U.S. PATENT DOCUMENTS

| | | | | |
|---|---|---|---|---|
| 6,645,429 B1 * | 11/2003 | Raniwala | .............. | B65B 55/027 422/305 |
| 2007/0140893 A1 * | 6/2007 | McVey | .................... | A61L 2/24 422/305 |

* cited by examiner

*Primary Examiner* — Monzer R Chorbaji
(74) *Attorney, Agent, or Firm* — McCarter & English, LLP

(57) ABSTRACT

A food processing facility having application apparatus located within the interior space of the food processing facility for applying a PAA solution to food, a mixing container for containing a PAA solution having a PAA solution concentration, with the mixing container connected to the application apparatus for delivering the PAA solution to the application apparatus, and a PAA gas sensor, located within the interior space, for sensing a PAA airborne concentration. An actuation control system connected to the PAA gas sensor is adapted to receive a measure of the PAA airborne concentration and, when the measure of the PAA airborne concentration exceeds a reference value, changes one or more of the PAA solution concentration of the PAA solution in the mixing container, the flow rate of the fresh air ventilation system, and the flow rate of the exhaust air system.

25 Claims, 3 Drawing Sheets

(51) Int. Cl.
*A61L 9/00* (2006.01)
*B01F 23/40* (2022.01)
*B01F 35/21* (2022.01)
*B01F 35/221* (2022.01)
*B01F 35/71* (2022.01)
*F24F 11/00* (2018.01)
*B01F 101/04* (2022.01)

PERACETIC ACID MONITORING AND CONTROL SYSTEM

CROSS-REFERENCE TO RELATED APPLICATION

This application claims the benefit of U.S. Provisional Application No. 63/071,443, filed Aug. 28, 2020.

BACKGROUND OF THE INVENTION

Field of the Invention

This invention relates to systems for monitoring and controlling concentrations of peracetic acid in disinfectant solutions and in the air of facilities where such solutions are utilized.

Description of the Related Art

Peracetic acid (also sometimes referred to as PAA or peroxyacetic acid) is used in the food and beverage industries as an antimicrobial agent, sanitizer and surface cleaner. In the case of meat and poultry processing facilities, PAA is used as a disinfectant to reduce bacterial contamination and spoilage. For example, in the case of poultry processing PAA can be applied to product positioned on a conveyor by means of multiple spray heads that discharge a PAA solution onto the product as it is conveyed past the spray heads. As another example, product can be immersed in a chill tank containing a PAA solution.

PAA is generally diluted in water to a concentration in the range of approximately 50 to 2,000 ppm when used in meat and poultry processing in the manner described above. While safe for contact at such concentrations, when PAA is airborne it may cause eye, nose, throat and respiratory irritation to humans. For this reason, the American Conference of Governmental Hygienists recommends a limit on airborne concentrations of PAA at 0.4 ppm as a 15-minute short term exposure limit.

The nature of PAA delivery in the meat and poultry processing facilities can make challenging the control of PAA airborne concentrations while maintaining delivery of PAA at desired concentration levels. For example, PAA undergoes an atomization in the course of spray nozzle delivery, which can result in PAA being airborne throughout the facility at points distant from the point of application, depending on facility ventilation. In addition, the movement of processing equipment and/or product on which has been applied PAA likewise can facilitate the spread of PAA in the air. As a result, the PAA airborne concentrations may exceed predetermined concentration limits in the production area to the prejudice of personnel in that area.

SUMMARY OF THE INVENTION

The present invention provides an efficient system for controlling PAA liquid and airborne concentrations in food processing facilities, in order to optimize disinfection performance, and minimize risk to facility personnel while at the same time potentially lowering facility down time due to excursions in PAA airborne concentration above pre-set ceilings.

In one aspect, the present invention is directed to a food processing facility having an interior space, comprising application apparatus located within the interior space for applying a PAA solution to food; a mixing container for containing a PAA solution having a PAA solution concentration, the mixing container connected to the application apparatus for delivering the PAA solution to the application apparatus; a water line connected to the mixing container for delivering feed water to the mixing container; and a PAA line connected to the mixing container for delivering PAA to the mixing container. There is also provided a control valve in one of the water line and the PAA line for varying respectively one of the amount of feed water and the amount of PAA delivered to the mixing container, and a first PAA gas sensor, located at a location within the interior space, for sensing a PAA airborne concentration. In addition, there is provided an actuation control system connected to the first PAA gas sensor and adapted to receive from the first PAA gas sensor a measure of the PAA airborne concentration sensed by the first PAA gas sensor and, when the measure of the PAA airborne concentration exceeds a first reference value, to actuate the control valve in one of the water line and the PAA line to reduce the PAA solution concentration of the PAA solution in the mixing container.

In another aspect, the present invention is directed to a method of controlling a PAA airborne concentration in a food processing facility having an interior space, comprising the steps of providing a PAA solution in a mixing container having a PAA solution concentration; applying at an application point the PAA solution from the mixing container to food; measuring with a PAA gas sensor the PAA airborne concentration at a location within the interior space and communicating a measure of the PAA airborne concentration to an actuation control system; changing, when the measure of the PAA airborne concentration exceeds a reference value, the PAA solution concentration in the mixing container under the direction of the actuation control system to provide a changed PAA solution in the mixing container having a reduced PAA solution concentration; and applying at the application point the changed PAA solution from the mixing container to food.

In a further aspect, the present invention is directed to a method of controlling a PAA solution concentration utilized in a food processing facility, comprising the steps of providing a PAA solution in a mixing container having a PAA solution concentration; applying at an application point the PAA solution from the mixing container to food; measuring with a PAA liquid sensor the PAA solution concentration and communicating a measure of the PAA solution concentration to an actuation control system; changing, when the measure of the PAA solution concentration differs from a reference value, the PAA solution concentration in the mixing container under the direction of the actuation control system to provide a changed PAA solution in the mixing container having a changed PAA solution concentration; and applying at the application point the changed PAA solution from the mixing container to food.

These and other aspects of the present invention are described in the drawings annexed hereto, and in the description of the preferred embodiments and claims set forth below.

DETAILED DESCRIPTION OF THE PREFERRED EMBODIMENTS

Figure 1:
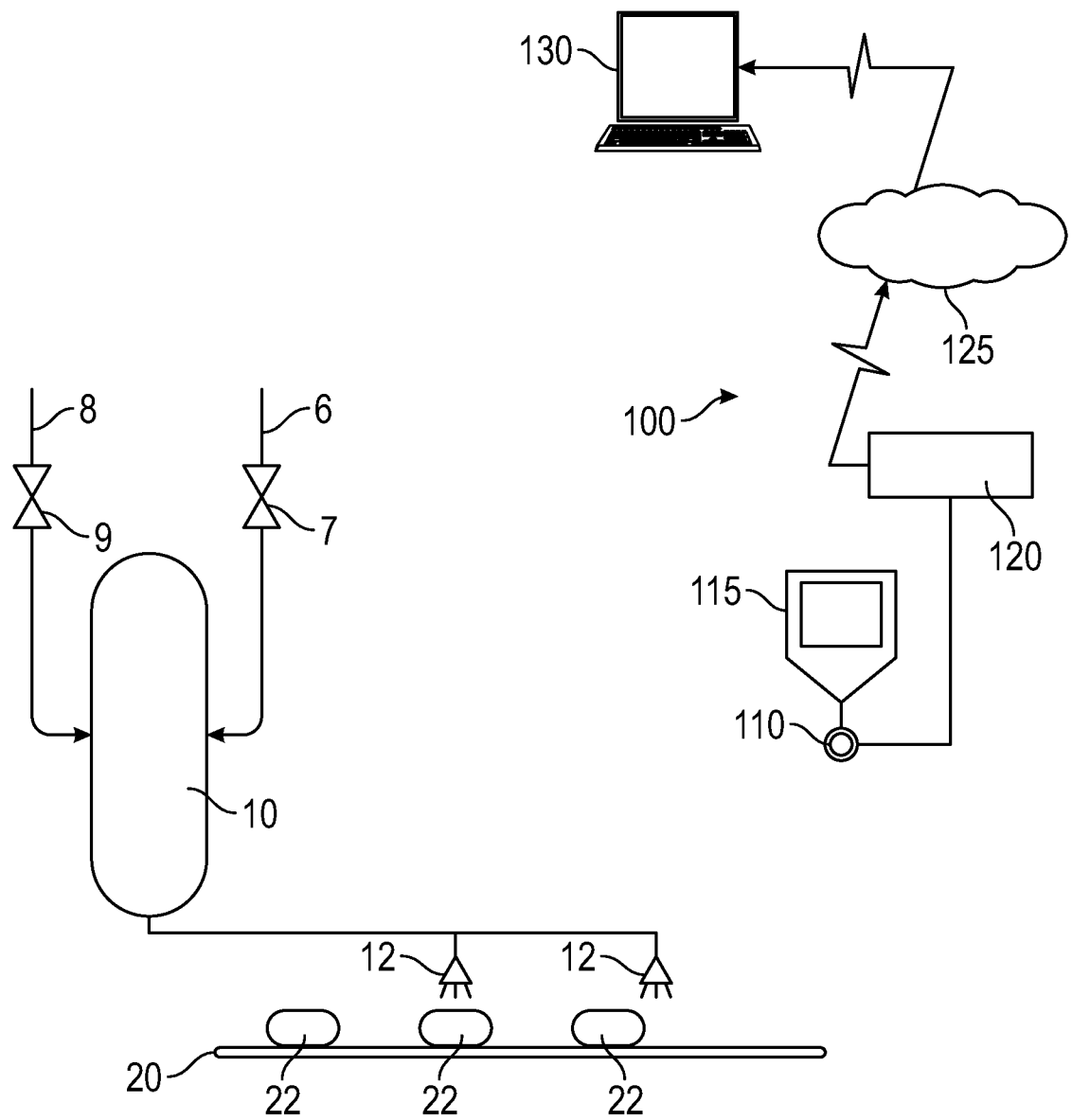
FIG. 1 is a schematic diagram of the monitoring system of the present invention in a processing facility.

FIG. 1 depicts a portion of a poultry production facility. As shown in the figure, discrete portions 22 of poultry product are moved on a conveyor 20 for processing and packaging. At one or more points, an aqueous solution of PAA is applied to the portions 22 of poultry product. In the embodiment shown the PAA solution is applied by means of overhead nozzles 12, which spray the PAA solution onto the portions 22 of poultry product. An alternative means of treatment is to dip the portions 22 of poultry product into a chill tank containing the PAA solution.

The PAA solution in the embodiment shown is delivered to the nozzles 12 from a mixing container 10, which in turn is supplied with water delivered from water line 6 and with PAA delivered from PAA line 8. PAA line 8 has a control valve 9 which varies the amount of PAA that enters mixing container 10, and water line 6 has a control valve 7 which varies the amount of water entering mixing container 10.

Water from water line 6 and PAA from PAA line 8 are periodically added to mixing container 10 at preselected addition times, or alternatively, on a continuous basis. In this disclosure, addition is assumed to take place at preselected times; however, the concepts described herein are equally applicable both to discrete and to continuous addition processes. By suitable adjustment of control valves 7 and 9, the PAA solution concentration (i.e., the PAA concentration in the aqueous PAA solution in mixing container 10) can be changed. Typically one or both of control valves 7 and 9 are adjusted so as to dilute the PAA solution concentration to be in the range of approximately from 50 ppm PAA to approximately 2,000 ppm PAA, and more particularly in the range of approximately from 1,200 ppm PAA to approximately 1,500 ppm PAA, especially to a PAA solution concentration of approximately 1,000 ppm PAA.

First Embodiment

As indicated above, the processing of poultry product in the manner just described will result in PAA being introduced into the atmosphere in the facilities in which processing occurs, which at sufficiently high levels can be hazardous to personnel working in the facility. To safeguard such personnel, there is provided in the first embodiment of the present invention a monitoring system 100, which as shown in FIG. 1 includes a PAA gas sensor 110, a local display 115, a data transmission unit 120 and a computer 130.

In particular, PAA gas sensor 110 senses the PAA airborne concentration (i.e., the PAA concentration in the atmosphere within the production facility in the vicinity of sensor head 110) and periodically transmits that information in digital form, along with a time stamp, an identifier such as a sensor head ID number, and the ambient temperature. The information is transmitted to data transmission unit 120 and, optionally, display 115. PAA gas sensor 110 can contain the requisite electronics and data memory for performing these functions, and preferably utilizes the Modbus communications protocol for the transmission of data.

As stated above, PAA gas sensor 110 is optionally connected to a display 115, which can be used for display of PAA airborne concentration readings. Display 115 if used generally is located proximate sensor head 110 in the facility in which processing occurs, and can include appropriate circuitry and programming to provide a display of PAA airborne concentration and optionally to produce an audible alarm in the event a ceiling limit on PAA airborne concentration is reached or exceeded. A suitable sensor head for PAA airborne measurement, and a suitable display for PAA concentration readings, are both available from Analytical Technology Inc., Saddleworth, UK.

In FIG. 1, data transmission unit 120 receives the information from PAA gas sensor 110 and sends it via a network 125 for display on computer 130. Network 125 can be one or more of a mobile phone wireless network, a local area wired or wireless network, a wide area wired or wireless network, etc., typically utilizing the Internet protocol suite. Computer 130 can be programmed to display the data in a desired format, and to provide an alert message or alarm in the event a ceiling limit on PAA airborne concentration is reached or exceeded and/or to provide multiple alert messages or alarms, each associated with a specific PAA airborne concentration, which are triggered as sensed PAA airborne concentration changes (especially increases). As one example, computer 130 can be programmed to generate an alert message or alarm when the PAA airborne concentration meets or exceeds 0.3 ppm PAA concentration. Such programming can additionally be adapted to process and store PAA and related data so as to provide historic PAA concentration data, variations with time and temperature, etc.

As an alternative to programming computer 130 to process and generate displays of PAA information, appropriate software for such processing and generating displays can be cloud-based, and include appropriate commercial cloud-based tools. A suitable cloud-based tool for data processing and display is the CDLSmartHub™ offered by Caption Data, Worcester, UK. In this alternative, computer 130 would in part serve as a display terminal for information generated and formatted as dictated by the cloud-based software, and to perform such computational tasks as the cloud-based software delegates to computer 130. Computer 130 can be placed at a location that is appropriate for the specific processing facility. For example, computer 130 can be located on the floor of the processing facility at the work area of environmental, health and safety personnel, or at the location of any governmental employees located on-site.

Although only one PAA gas sensor 110 is depicted, since the PAA airborne concentration level can vary within a facility depending on environmental and locational factors such as distance from the product stream, it is preferred to utilize multiple PAA gas sensors 110, each with a different identifier. The PAA gas sensors 110 are positioned apart from each other at a suitable radius, for example twenty feet. In one embodiment, each such sensor head 110 is connected to a respective data transmission unit 120, and is independent of other PAA gas sensors 110 in the processing facility. The PAA airborne concentration level at each PAA gas sensor 110 can be displayed on computer 130, and the associated software can be adapted to permit the viewer to step through the readings of each PAA gas sensor 110, and/or develop for display (as an example) PAA concentration level facility maps, both on a real-time basis and on a historical basis to show changes in PAA concentration level(s) over time.

Second Embodiment

Figure 2A:
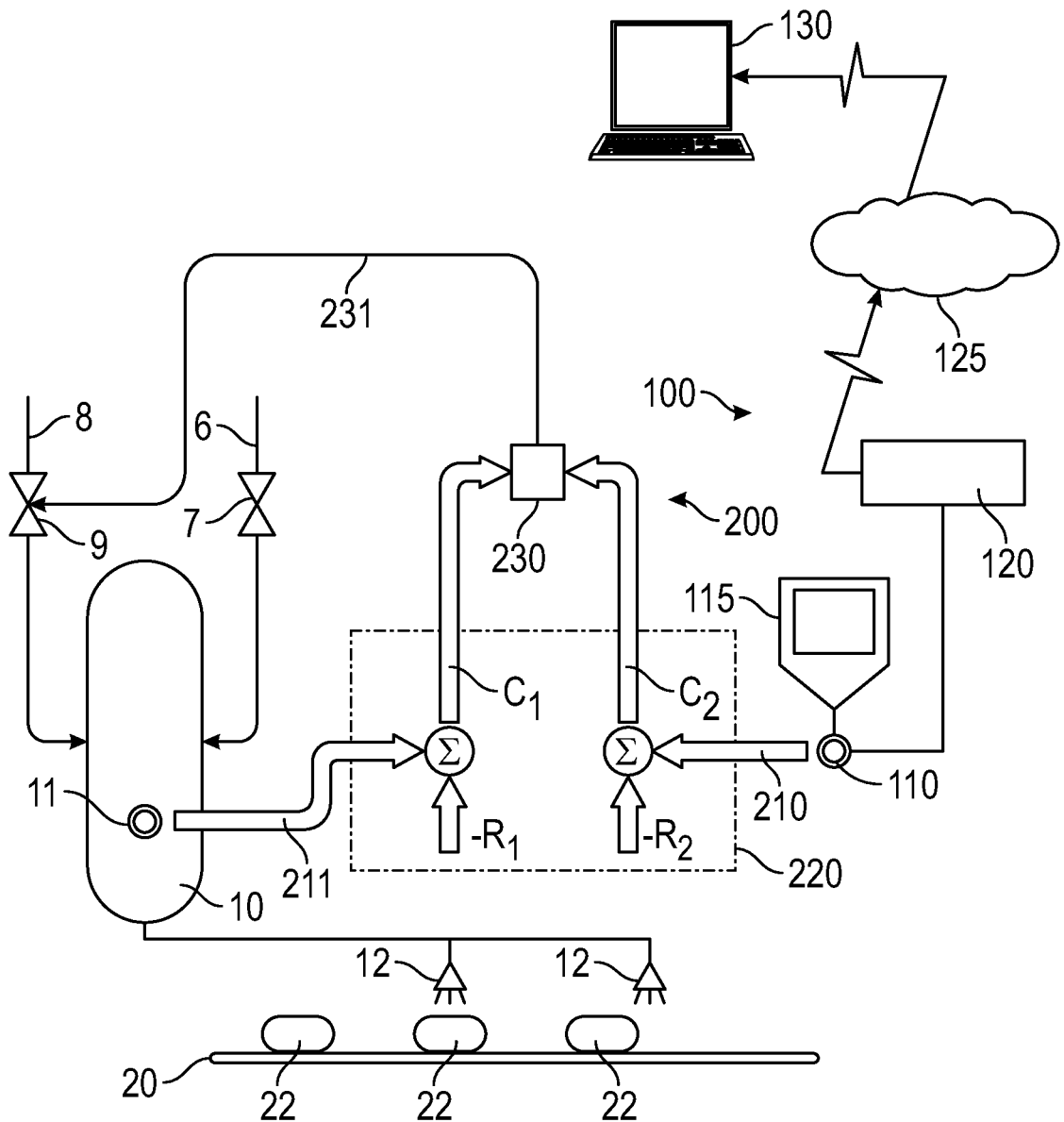
FIG. 2A is a schematic diagram of an embodiment of the monitoring and control system of the present invention in a processing facility.

FIG. 2A depicts a second embodiment of the present invention, in which monitoring system 100 is functionally linked to a control system 200. Control system 200 includes an evaluation module 220 and an actuation module 230. Control system 200 is characterized by two related closed-loop feedback systems: (1) a closed-loop feedback system in which control system 200 responds to fluctuations in PAA solution concentration (i.e., the PAA concentration in the aqueous PAA solution in mixing container 10) to vary the PAA solution concentration; and (2) a closed-loop feedback system in which control system 200 responds to fluctuations in PAA airborne concentration levels to vary the PAA solution concentration.

Referring to the embodiment shown in FIG. 2A, PAA gas sensor 110 provides data to both monitoring system 100 and to control system 200. More particularly, PAA gas sensor 110 is linked both to local display 115 and data transmission unit 120 of monitoring system 100, and also to evaluation module 220 of control system 200. Specifically, a data link 210 communicates PAA airborne concentration levels from PAA gas sensor 110 to evaluation module 220. In addition, there is provided a container sensor head 11 in mixing container 10, which is also linked to evaluation module 220 via a data link 211, to communicate the PAA solution concentration in mixing container 10 to evaluation module 220. In turn, actuation module 230 is linked to a solenoid on control valve 9, via control link 231, and exercises control over one process variable, specifically the amount of PAA added into mixing container 10, by adjustment of control valve 9.

Data links 210 and 211, and control link 231, each can be a wired or wireless connection, as may be preferred. Also, particularly as to data link 210, there need not be a point-to-point direct connection path between PAA gas sensor 110 and evaluation module 220, as the path of data link 210 can be through data transmission unit 120 and/or computer 130, where intermediate processing on the data can be performed prior to being received at evaluation module 220, in accordance with preference. Evaluation module 220 can be an analog or electronic hard-wired controller, or a programmable digital system that utilizes one or more microprocessors to execute a stored program or programs to perform the operations described herein.

Evaluation module 220 can be utilized to maintain or adjust the PAA solution concentration. Referring to FIG. 2A, the PAA solution concentration is received over data link 211 and periodically compared by evaluation module 220 to a reference PAA concentration $R_1$. If the received PAA solution concentration is above or below $R_1$ by more than a respective predetermined ceiling or floor limit, then evaluation module 220 generates a correction signal $C_1$ to actuation module 230. Actuation module 230 in turn generates a control signal, transmitted over control link 231, which actuates the solenoid on control valve 9 to appropriately vary the amount of PAA added into mixing container 10.

For example, if the desired PAA solution concentration in mixing container 10 is 1,000 ppm, and container sensor head 11 indicates a concentration level of 1,100 ppm in mixing container 10 (which, in this example, is above the predetermined ceiling limit), then evaluation module 220 generates a correction signal $C_1$ to actuation module 230, which in turn generates a control signal to actuate the solenoid on control valve 9 over control link 231 to reduce the amount of PAA to be added to mixing container 10 at the next addition time. Since in this example the amount of water to be added at the next addition time is not changed, the result will be to reduce the PAA concentration in mixing container 10. In turn, the solution being sprayed by nozzles 12 will be more dilute, with the intended goal of reducing the PAA airborne concentration level.

Likewise, if container sensor head 11 indicates a PAA concentration in mixing container 10 of less than 1,000 ppm (which, in this example, is below the predetermined floor limit), then evaluation module 220 generates a correction signal to actuation module 230, which in turn generates a control signal $C_1$ to actuate the solenoid on control valve 9 to increase the amount of PAA to be added at the next addition time to mixing container 10. Thus, as a general matter, control system 200 can be utilized to reduce the possibility of the PAA solution concentration in mixing container 10 dropping below a level that is necessary or desirable to insure that processing of portions 22 is carried out in sanitary conditions.

While the foregoing assumes that the PAA solution concentration is adjusted by changing the amount of PAA to be added to mixing container 10 at the next addition time, the same outcome can be achieved by a control line linking a solenoid on control valve 7 to actuation module 230, and changing the amount of water to be added to mixing container at the next addition time, in accordance with preference. Likewise, both the amount of PAA and the amount of water can be simultaneously adjusted, again as preferred.

Notably, in addition to maintaining or adjusting the PAA solution concentration level in mixing container 10, evaluation module 220 can be utilized to control PAA airborne concentration levels. Specifically, the PAA airborne concentration level is received over data link 210 and periodically compared by evaluation module 220 to a reference PAA airborne concentration $R_2$, the maximum allowed airborne concentration. If the received PAA airborne concentration level exceeds $R_2$, then evaluation module 220 generates a correction signal $C_2$ to actuation module 230, which in turn generates a control signal over control link 231 to actuate the solenoid on control valve 9 to reduce the amount of PAA to be added to mixing container 10 at the next addition time.

For example, if the maximum allowed airborne concentration $R_2$ is set at 0.3 ppm and PAA gas sensor 110 indicates a PAA airborne concentration of 0.34 ppm, then evaluation module 220 generates a correction signal to actuation module 230, which in turn generates a control signal over control link 231 to actuate the solenoid on control valve 9 to reduce the amount of PAA to be added to mixing container 10 at the next addition time. Since in this example the amount of water to be added into mixing container 10 is not changed, the result will be to reduce the PAA solution concentration in mixing container 10. In turn, the solution being sprayed by nozzles 12 will be more dilute, with the intended goal of reducing the PAA airborne concentration level. At the same time, given that evaluation module 220 also monitors the PAA solution concentration in mixing container 10, evaluation module 220 can be adapted to insure that solution dilution to reduce PAA airborne concentration does not cause the PAA solution concentration to drop below a lower limit set to insure that processing is carried out in sanitary conditions.

Third Embodiment

Figure 2B:
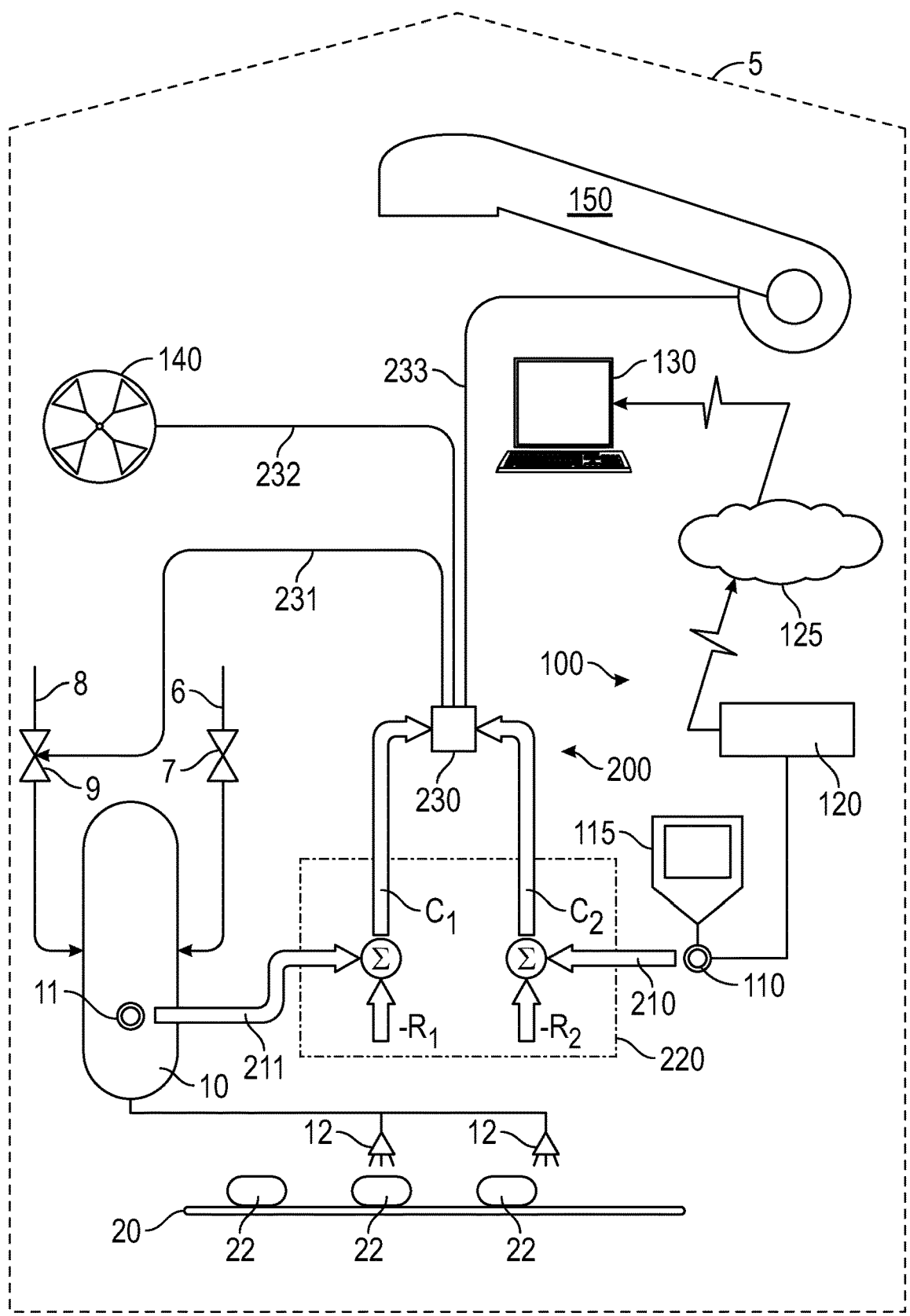
FIG. 2B is a schematic diagram of another second embodiment of the monitoring and control system of the present invention in a processing facility

FIG. 2B depicts a third embodiment of the present invention, in which monitoring system 100 is functionally linked to control system 200 in order to respond to fluctuations in PAA airborne concentration levels by varying one or more of the PAA solution concentration, the exhaust air flow from the facility and the fresh air flow introduced into the facility. In FIG. 2B, the poultry processing equipment is located within a boundary 5 (representing a building housing a poultry production facility), which separates the atmosphere of the production facility from the outside environment. Likewise, monitoring system 100 and control system 200 are located within boundary 5. Outside air is introduced into and within boundary 5 by a fresh air ventilation system 150, and interior air is removed from within boundary 5 to the outside environment by exhaust air system 140.

In the third embodiment of FIG. 2B, actuation module 230 exercises control over one process variable, the amount of PAA added to mixing container 10 (as in the second embodiment of FIG. 2A), and over two environmental variables, namely the exhaust air flow rate and the fresh air flow rate. In particular, actuation module 230 is linked to the solenoid on control valve 9 via control link 231, as in the FIG. 2A embodiment, in order to control the amount of PAA added to mixing container 10 by adjustment of control valve 9. In addition, actuation module 230 is also linked, via control link 232, to a power controller associated with exhaust air system 140, in order to control the exhaust air flow rate by adjustment of, for example, the rotational speed of an exhaust fan in exhaust air system 140. Still further, actuation module 230 is linked, via control link 233, to a power controller associated with fresh air ventilation system 150, in order to control the fresh air flow rate by adjustment of, for example, the rotational speed of a centrifugal air blower in fresh air ventilation system 150. Each of control links 231, 232 and 233 can be a wired or wireless connection, as may be preferred.

In the operation of the third embodiment, evaluation module 220 receives the PAA airborne concentration level over data link 210 and periodically compares it to reference PAA airborne concentration $R_2$. If the received PAA airborne concentration level exceeds a maximum allowed airborne concentration $R_2$, then evaluation module 220 generates a correction signal $C_2$ to actuation module 230. In this embodiment, that correction signal $C_2$ can generate remedial action in a number of alternative ways, in accordance with the programming of evaluation module 220. As a first alternative, the correction signal $C_2$ can instruct actuation module 230 to generate control signals over control links 231-233 to simultaneously actuate the solenoid on control valve 9, the power controller associated with exhaust air system 140 and the power controller associated with fresh air ventilation system 150. As a second alternative, the correction signal $C_2$ can instruct actuation module 230 to actuate less than all of the foregoing, depending on the magnitude of the PAA airborne solution concentration level, both alone and as compared to prior readings thereof.

As one example within scope of the second alternative, if the maximum allowed airborne concentration $R_2$ is set at 0.3 ppm and PAA gas sensor 10 indicates a PAA airborne concentration of 0.34 ppm, then following a comparison carried out at time $T_1$ evaluation module 220 generates a first correction signal $C_2$ to actuation module 230, which in turn generates a control signal over control line 231 only to actuate the solenoid on control valve 9 to reduce the amount of PAA added to mixing container 10 at the next addition time, as in the second embodiment. Since the amount of water added to mixing container 10 is not changed, the result will be to reduce the PAA solution concentration in mixing container 10, and the solution being applied by nozzles 12 will be more dilute. Then at a time $T_2$ following time $T_1$, evaluation module 220 again performs a comparison of the PAA airborne concentration with the 0.3 ppm ceiling level. If the PAA airborne concentration has been reduced to below 0.3 ppm, no further action is taken. However, if the PAA airborne concentration still exceeds the ceiling level, then evaluation module 220 can generate a second correction signal $C_2$ to actuation module 230, causing it to generate a control signal over control line 232 to actuate the power controller associated with exhaust air system 140 to increase the exhaust air flow rate, or even generate a third correction signal $C_2$ to actuation module 230, causing it to generate control signals over control lines 232 and 233 to actuate both the power controller associated with exhaust air system 140 to increase the exhaust air flow rate, and also the power controller associated with fresh air ventilation system 150 to increase the fresh air flow rate.

The foregoing detailed description is for illustration only and is not to be deemed as limiting the inventions, which are defined in the appended claims.

What is claimed is:

1. A food processing facility having an interior space, comprising:
   (a) application apparatus located within the interior space for applying a PAA solution to food;
   (b) a mixing container for containing a PAA solution having a PAA solution concentration, the mixing container connected to the application apparatus for delivering the PAA solution to the application apparatus;
   (c) a water line connected to the mixing container for delivering feed water to the mixing container;
   (d) a PAA line connected to the mixing container for delivering PAA to the mixing container;
   (e) a control valve in one of the water line and the PAA line for varying respectively one of the amount of feed water and the amount of PAA delivered to the mixing container;
   (f) a first PAA gas sensor, located at a first location within the interior space, for sensing a PAA airborne concentration; and
   (g) an actuation control system connected to the first PAA gas sensor and adapted to receive from the first PAA gas sensor a measure of the PAA airborne concentration sensed by the first PAA gas sensor and, when the measure of the PAA airborne concentration exceeds a first reference value, to actuate the control valve in one of the water line and the PAA line to reduce the PAA solution concentration of the PAA solution in the mixing container.

2. The food processing facility of claim 1, wherein the actuation control system comprises:
   i. i. an evaluation unit connected to the first PAA gas sensor and adapted to receive from the first PAA gas sensor a measure of the PAA airborne concentration sensed by the first PAA gas sensor and to generate a first correction signal when the measure of the PAA airborne concentration exceeds the first reference value;
   ii. ii. an actuation unit connected to the evaluation unit and adapted to generate a first control signal upon receipt of the first correction signal; and
   iii. iii. a solenoid connected to the control valve for varying the amount of one or both of the amount of feed water and the amount of PAA delivered to the mixing container in accordance with the first control signal.

3. The food processing facility of claim 1, further comprising one or more other PAA gas sensors for sensing a PAA airborne concentration, the one or more other PAA gas sensors respectively located at one or more other locations within the interior space different from the first location; and wherein the actuation control system is connected to the one or more other PAA gas sensors and is further adapted to receive from the one or more other PAA gas sensors a measure of the PAA airborne concentration respectively sensed by the one or more other PAA gas sensors and, when the measure of the PAA airborne concentration of any of the first PAA gas sensor and the one or more other PAA gas sensors exceeds the first reference value, to actuate the control valve to reduce the PAA solution concentration of the PAA solution in the mixing container.

4. The food processing facility of claim 1, wherein the feed water comprises an aqueous fluid stream.

5. The food processing facility of claim 4, wherein a source of the aqueous fluid stream is a feed water system for decontamination of food selected from the group consisting of meats, other proteins, vegetables and starches.

6. The food processing facility of claim 5, wherein the first reference value is set at a level to minimize PAA health risk to personnel.

7. The food processing facility of claim 1, wherein the actuation control system is adapted to periodically compare, at select time intervals, the measure of the PAA airborne concentration with the first reference value, to determine if the measure of the PAA airborne concentration exceeds the first reference value.

8. The food processing facility of claim 1, further comprising:
(h) a PAA liquid sensor for sensing the concentration of the PAA solution in the mixing container; and
wherein the actuation control system is additionally connected to the PAA liquid sensor and is adapted to receive from the PAA liquid sensor a measure of the PAA solution concentration in the mixing container, and, when the measure of the PAA solution concentration differs from a second reference value, to actuate the control valve to change the PAA solution concentration of the PAA solution in the mixing container.

9. The food processing facility of claim 1, further comprising:
(h) a fresh air ventilation system for introducing outside air to the interior space of the food processing facility; and
wherein the actuation control system is further adapted to:
(i) actuate the control valve to change the PAA solution concentration of the PAA solution in the mixing container when the measure of the PAA airborne concentration exceeds the first reference value at a first time, and (ii) increase the flow rate of the fresh air ventilation system when the measure of the PAA airborne concentration exceeds the first reference value at a second time later than the first time.

10. The food processing facility of claim 9, further comprising:
(i) an exhaust air system for removing interior air from the interior space of the food processing facility; and
wherein the actuation control system is further adapted to:
(i) actuate the control valve to reduce the PAA solution concentration of the PAA solution in the mixing container, and (ii) increase the flow rate of the fresh air ventilation system, and (iii) increase the flow rate of the exhaust air system, when the measure of the PAA airborne concentration exceeds the first reference value.

11. The food processing facility of claim 1, further comprising:
(h) a fresh air ventilation system for introducing outside air to the interior space of the food processing facility; and
wherein the actuation control system is further adapted to both: (i) actuate the control valve to reduce the PAA solution concentration of the PAA solution in the mixing container, and (ii) increase the flow rate of the fresh air ventilation system, when the measure of the PAA airborne concentration exceeds the first reference value.

12. The food processing facility of claim 1, further comprising:
(h) a fresh air ventilation system for introducing outside air to the interior space of the food processing facility;
(i) an exhaust air system for removing interior air from the interior space of the food processing facility; and
wherein the actuation control system is further adapted to:
(i) actuate the control valve to reduce the PAA solution concentration of the PAA solution in the mixing container when the measure of the PAA airborne concentration exceeds the first reference value at a first time, and (ii) increase at least one of: (A) the flow rate of the fresh air ventilation system, or (B) the flow rate of the exhaust air system, when the measure of the PAA airborne concentration exceeds the first reference value at a second time later than the first time.

13. The food processing facility of claim 12, wherein the actuation control system is further adapted to increase both of: (A) the flow rate of the fresh air ventilation system, and (B) the flow rate of the exhaust air system, when the measure of the PAA airborne concentration exceeds the first reference value at a second time later than the first time.

14. A food processing facility having an interior space, comprising:
(a) application apparatus located within the interior space for applying a PAA solution to food;
(b) a PAA gas sensor, located within the interior space for sensing a PAA airborne concentration;
(c) a fresh air ventilation system for introducing outside air to the interior space of the food processing facility;
(d) an actuation control system connected to the PAA gas sensor adapted to receive from the PAA gas sensor a measure of the PAA airborne concentration sensed by the PAA gas sensor and to increase the flow rate of the fresh air ventilation system when the measure of the PAA airborne concentration exceeds a reference value; and
(e) a mixing container for containing the PAA solution having a PAA solution concentration, the mixing container connected to the application apparatus within the interior space for delivering the PAA solution to the application apparatus, a water line connected to the mixing container for delivering feed water to the mixing container, and a PAA line connected to the mixing container for delivering PAA to the mixing container, wherein the actuation control system is adapted to actuate a control valve in one of the water line and the PAA line to reduce the PAA solution concentration of the PAA solution in the mixing container when the measure of the PAA airborne concentration exceeds the reference value.

15. The food processing facility of claim 14, further comprising:
(e) an exhaust air system for removing interior air from the interior space of the food processing facility; and
wherein the actuation control system is further adapted to:
(i) increase the flow rate of the fresh air ventilation system when the measure of the PAA airborne concentration exceeds the first reference value at a first time, and (ii) increase the flow rate of the exhaust air system when the measure of the PAA airborne concentration exceeds the first reference value at a second time different from the first time.

16. The food processing facility of claim 15, wherein the second time is later than the first time.

17. The food processing facility of claim 15, wherein the first time is later than the second time.

18. The food processing facility of claim 14, further comprising:
   (e) an exhaust air system for removing interior air from the interior space of the food processing facility; and
   wherein the actuation control system is further adapted to increase both: (i) the flow rate of the fresh air ventilation system and (ii) the flow rate of the exhaust air system, when the measure of the PAA airborne concentration exceeds the reference value.

19. A food processing facility having an interior space, comprising:
   (a) application apparatus located within the interior space for applying a PAA solution to food;
   (b) a PAA gas sensor, located within the interior space for sensing a PAA airborne concentration;
   (c) an exhaust air system for removing interior air from the interior space of the food processing facility;
   (d) an actuation control system connected to the PAA gas sensor adapted to receive from the PAA gas sensor a measure of the PAA airborne concentration sensed by the PAA gas sensor and to increase the flow rate of the exhaust air system, when the measure of the PAA airborne concentration exceeds a reference value; and
   (e) a mixing container for containing the PAA solution having a PAA solution concentration, the mixing container connected to an application apparatus within the interior space for delivering the PAA solution to the application apparatus, a water line connected to the mixing container for delivering feed water to the mixing container, and a PAA line connected to the mixing container for delivering PAA to the mixing container, wherein the actuation control system is adapted to actuate a control valve in one of the water line and the PAA line to reduce the PAA solution concentration of the PAA solution in the mixing container when the measure of the PAA airborne concentration exceeds the reference value.

20. The food processing facility of claim 19, further comprising:
   (e) a mixing container for containing a PAA solution having a PAA solution concentration, the mixing container connected to the application apparatus for delivering the PAA solution to the application apparatus;
   (f) a water line connected to the mixing container for delivering feed water to the mixing container;
   (g) a PAA line connected to the mixing container for delivering PAA to the mixing container;
   (h) a control valve in one of the water line and the PAA line for varying respectively one of the amount of feed water and the amount of PAA delivered to the mixing container; and
   wherein the actuation control system is further adapted to both: (i) increase the flow rate of the exhaust air system when the measure of the PAA airborne concentration exceeds the first reference value at a first time; and (ii) actuate the control valve to reduce the PAA solution concentration of the PAA solution in the mixing container, when the measure of the PAA airborne concentration exceeds the first reference value at a second time later than the first time.

21. The food processing facility of claim 19, further comprising:
   (e) a mixing container for containing a PAA solution having a PAA solution concentration, the mixing container connected to the application apparatus for delivering the PAA solution to the application apparatus;
   (f) a water line connected to the mixing container for delivering feed water to the mixing container;
   (g) a PAA line connected to the mixing container for delivering PAA to the mixing container;
   (h) a control valve in one of the water line and the PAA line for varying respectively one of the amount of feed water and the amount of PAA delivered to the mixing container; and
   wherein, when the measure of the PAA airborne concentration exceeds the reference value, the actuation control system is further adapted to both: (i) actuate the control valve to reduce the PAA solution concentration of the PAA solution in the mixing container, and (ii) increase the flow rate of the exhaust air system.

22. A food processing facility having an interior space, comprising:
   (a) application apparatus located within the interior space for applying a PAA solution to food;
   (b) a mixing container for the PAA solution, the mixing container connected to the application apparatus for delivering PAA solution to the application apparatus;
   (c) a water line connected to the mixing container for delivering feed water to the mixing container;
   (d) a PAA line connected to the mixing container for delivering PAA to the mixing container, the PAA line;
   (e) a control valve in one of the water line and the PAA line for varying respectively one of the amount of feed water and the amount of PAA delivered to the mixing container;
   (f) a PAA liquid sensor for sensing the PAA solution concentration in the mixing container;
   (g) an actuation control system connected to the PAA liquid sensor and adapted to receive from the PAA liquid sensor a measure of the PAA solution concentration in the mixing container sensed by the PAA liquid sensor and to actuate the control valve to change the PAA solution concentration in the mixing container when the measure of the PAA solution concentration differs from a reference value.

23. A food processing facility having an interior space, comprising:
   (a) application apparatus located within the interior space for applying a PAA solution to food;
   (b) a mixing container for the PAA solution, the mixing container connected to the application apparatus for delivering PAA solution to the application apparatus;
   (c) a water line connected to the mixing container for delivering feed water to the mixing container;
   (d) a PAA line connected to the mixing container for delivering PAA to the mixing container;
   (e) a PAA gas sensor, located at a first location within the interior space, for sensing a PAA airborne concentration;
   (f) a data transmission unit connected to and adapted to receive from the first PAA gas sensor a measure of the PAA airborne concentration;
   (g) a display unit connected over a network to the data transmission unit and adapted for displaying information related to the measure of the PAA airborne concentration sensed by the PAA gas sensor; and (h) an actuation control system connected to the PAA gas sensor and adapted to receive from the PAA gas sensor a measure of the PAA airborne concentration sensed by the PAA gas sensor and, when the measure of the PAA airborne concentration exceeds a reference value, to actuate a control valve in one of the water line and the PAA line to reduce the PAA solution concentration of the PAA solution in the mixing container.

24. The food processing facility of claim 23, further comprising one or more other PAA gas sensors for sensing a PAA airborne concentration, the one or more other PAA gas sensors respectively located at one or more other locations within the interior space different from the first location; one or more other data transmission units respectively connected to the one or more PAA gas sensors and adapted to receive therefrom a measure of the PAA airborne concentration sensed by the respective PAA gas sensor; and wherein the display unit is further adapted for displaying information related to the measure of the PAA airborne concentration received from each of the one or more other PAA gas sensors.

25. The food processing facility of claim 23, wherein the display unit is further adapted for displaying plural alert messages, each of such plural alert messages associated with a different PAA airborne concentration.

* * * * *